US00PP21065P2

(12) United States Plant Patent
Ichie

(10) Patent No.: US PP21,065 P2
(45) Date of Patent: Jun. 15, 2010

(54) ***HYDRANGEA* PLANT NAMED 'WHITE KING'**

(50) Latin Name: *Hydrangea macrophylla*
Varietal Denomination: White King

(76) Inventor: Toyokazu Ichie, 3-46 Hongou, Kakegawa-city, Shizuoka (JP) 436-0111

( * ) Notice: Subject to any disclaimer, the term of this patent is extended or adjusted under 35 U.S.C. 154(b) by 0 days.

(21) Appl. No.: 12/383,749

(22) Filed: Mar. 27, 2009

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent L Bell
(74) *Attorney, Agent, or Firm*—Penny J. Aguirre

(57) ABSTRACT

A new cultivar of *Hydrangea macrophylla* named 'White King' that is characterized by its very early blooming habit, its ability to re-bloom on new growth after deadheading, its consistently well-formed, large-sized inflorescences that are white in color and are resistant to sun scorching under high light intensity, its foliage that is resistant to powdery mildew, and its compact growth habit resulting in low maintenance.

2 Drawing Sheets

Botanical classification: *Hydrangea macrophylla.*
Varietal denomination: 'White King'.

BACKGROUND OF THE INVENTION

The present invention relates to a new and distinct cultivar of *Hydrangea macrophylla* and will be referred to hereafter by its cultivar name, 'White King'. 'White King' represents a new Bigleaf *Hydrangea*, a deciduous shrub grown for landscape use and for use as a potted plant in the lightly shaded landscape.

'White King' was derived from an ongoing controlled breeding program of the Inventor that focuses on obtaining new varieties of *Hydrangea* for landscape and container use. 'White King' derived from an open pollination of proprietary *Hydrangea macrophylla* selection No. H3-11 (not patented) made in June of 1998 in Shizuoka, Japan. 'White King' was selected as a single unique plant amongst the progeny in June of 1999.

Asexual reproduction of the new cultivar was first accomplished by softwood stem cuttings in Shizuoka, Japan in February of 2007 by the Inventor. The characteristics of this cultivar have been determined to be stable and are reproduced true to type in successive generations.

SUMMARY OF THE INVENTION

The following traits have been repeatedly observed and represent the characteristics of the new cultivar as observed in Shizuoka, Japan and Niagara on the Lakes, Ontario, Canada. These attributes in combination distinguish 'White King' as a unique cultivar of *Hydrangea macrophylla.*

1. 'White King' is a very early bloomer and removal of spent blooms results in a long season of repeat bloom from early June to October in Niagara on the Lake, Ontario, Canada.
2. 'White King' has consistently well-formed, large sized inflorescences that are white in color and are resistant to sun scorch when grown in areas with high light intensity.
3. 'White King' exhibits a compact growth habit resulting in a low level of plant maintenance.

4. 'White King' has foliage that exhibits a high level of high resistance to powdery mildew.
5. 'White King' is hardy at least to U.S.D.A. Zone 5b.

'White King' differs from its female parent plant, No. H3-11, in having a longer and earlier blooming habit and a greater level of resistance to sun scorch and powdery mildew. The new cultivar of *Hydrangea* can be compared to *Hydrangea macrophylla* 'Madame Emile Mouillère', (syn. 'Sedgewicks White', not patented) which is similar in having pure white flowers and a repeating blooming habit, however 'Madame Emile Mouillère' differs in having serrated sepal margins, in being highly susceptible to scorch under high light conditions and in having a more open and less compact plant habit. 'White King' can also be compared to the cultivar 'Annabelle', which is similar in having white flowers, rounded flower heads and a small plant size, however 'Annabelle' is a cultivar of *Hydrangea arborescens* and has a more open plant habit.

BRIEF DESCRIPTION OF THE DRAWINGS

The accompanying colored photographs illustrate the overall appearance and distinct characteristics of the new *Hydrangea*. The photographs were taken of two year-old plants of 'White King' as grown in a greenhouse in one-gallon containers in Shizuoka, Japan.

Figure 1:
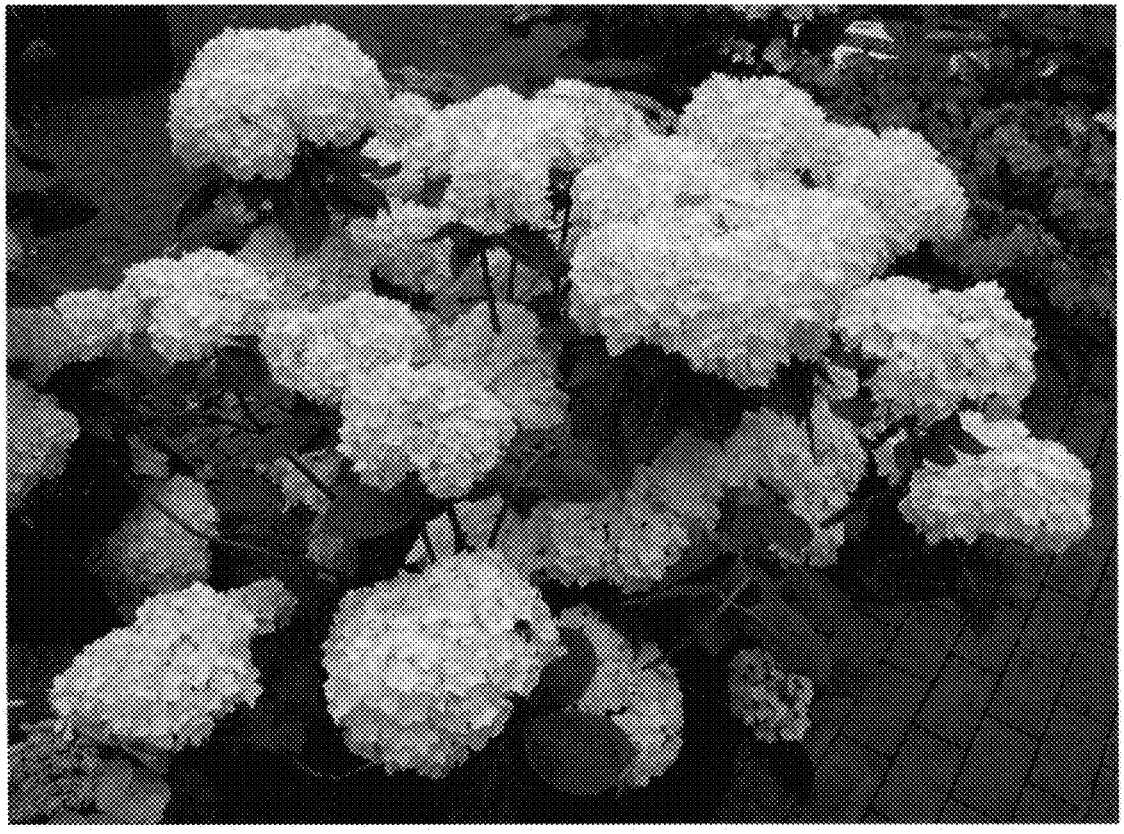
FIG. 1 was taken of 3 plants and illustrates the plant habit, foliage coloration and flowering habit.
Figure 2:
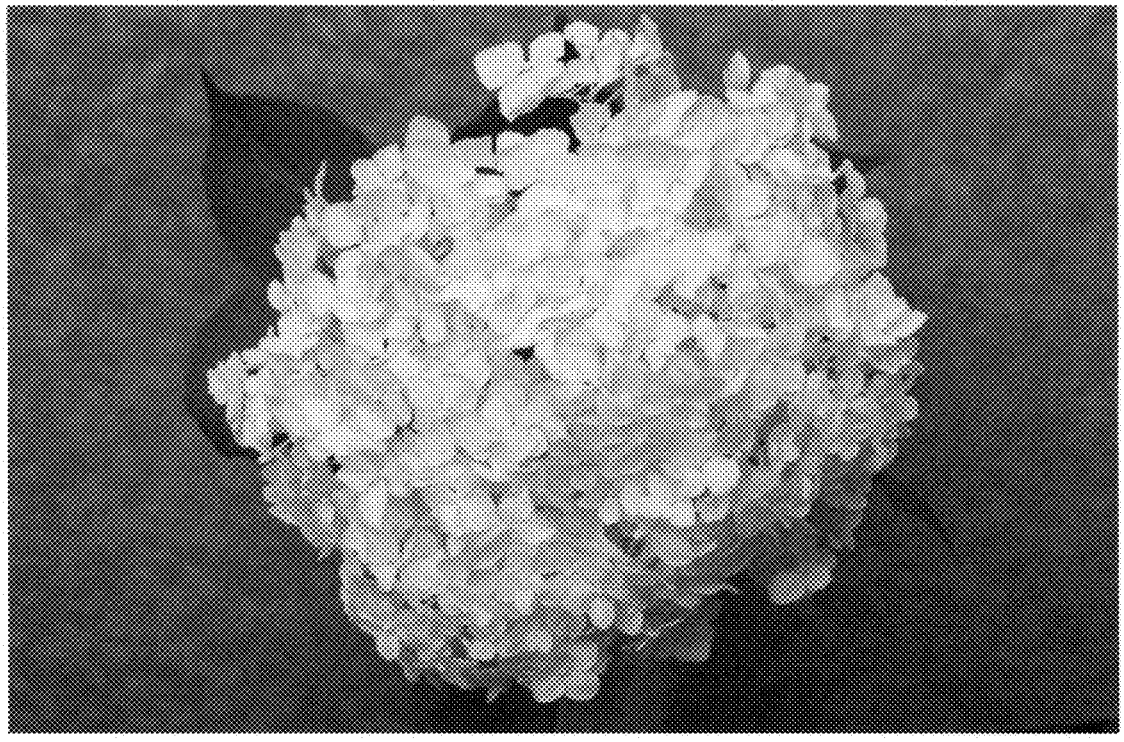

The photograph in FIG. 2 depicts a single inflorescence.

Figure 3:
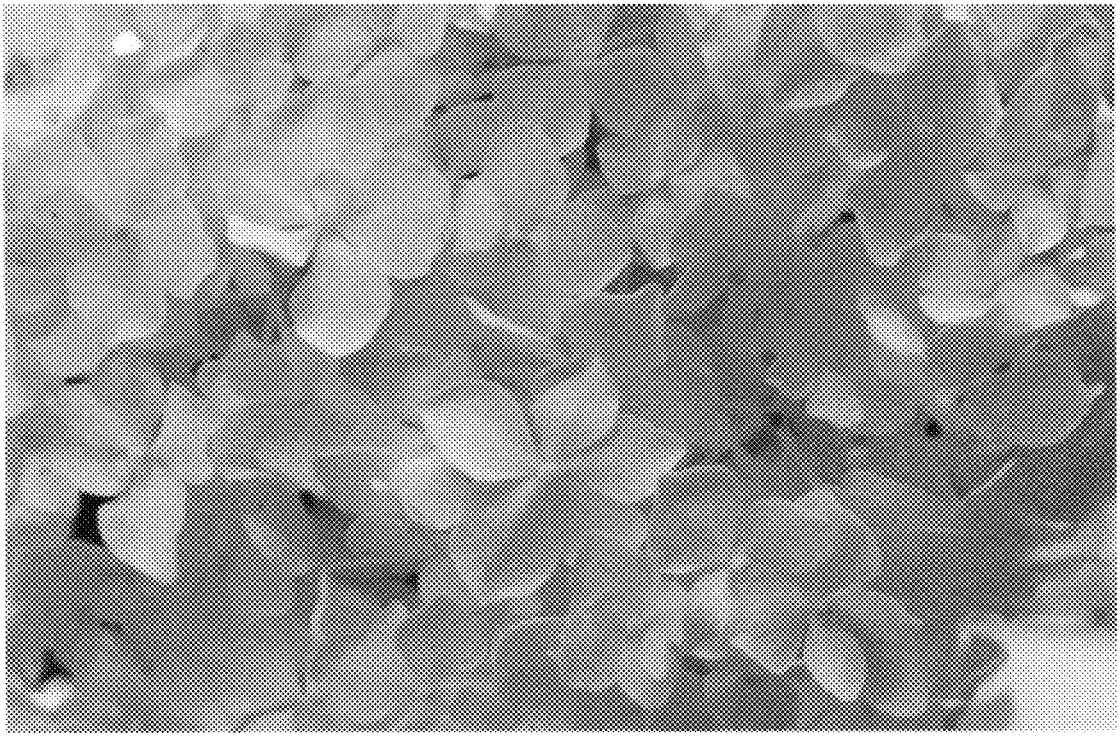

The photograph in FIG. 3 provides a close-up view of the fully open inflorescence.

The colors in the photographs are as close as possible with the digital photography and printing techniques utilized and the color codes in the detailed botanical description which accurately describe the new *Hydrangea.*

BOTANICAL DESCRIPTION OF THE PLANT

The following is a detailed description of 2 year-old plants of the new cultivar as grown in one-gallon containers under greenhouse conditions, in Shizuoka, Japan. Phenotypic differences may be observed with variations in environmental, climatic, and cultural conditions. The color determination is in accordance with the 2007 R.H.S. Colour Chart of The Royal Horticultural Society, London, England, except where general color terms of ordinary dictionary significance are used.

Commercial classification: Bigleaf *hydrangea*, Hortensia type.

General description:

*Blooming period.*—Early season bloomer, removal of spent blooms results in repeat bloom from early June to October in Shizuoka, Japan.

*Plant habit.*—Broadly upright, compact and requires low maintenance to retain size, deciduous shrub.

*Height and spread.*—Reaches about 70 cm in height and spread in the landscape.

*Cold hardiness.*—At least to U.S.D.A. Zone 5b.

*Culture.*—Grows best in moist but well-drained, humus-rich soil in full sun or partial shade with protection from high winds, no sun scorch has been observed when grown in trial areas with high light intensity.

*Diseases resistance.*—Has been observed to show a high level of resistance to powdery mildew.

*Root description.*—Fine.

Growth and propagation:

*Propagation.*—Softwood stem cuttings.

*Growth rate and vigor.*—Moderate.

Stem description:

*Stem shape.*—Round, solid.

*Stem strength.*—Very strong.

*Stem color.*—New growth; a blend of 144A and 144B with lenticels 152A, woody; blend of 165A and N199C.

*Stem size.*—Average of 20.6 cm (to base of inflorescence), average of 8 mm in width.

*Stem surface.*—Glabrous, dull, very sparsely covered with lenticels; about 5 per square cm, about 0.5 mm in length and width, becoming bark-like with age.

*Internode length.*—Average of 7.1 cm.

*Branching.*—A single dormant stem will produce an average of 2 lateral branches, sublateral branching is determined by pinching; 2stems develop per pinched node.

Foliage description:

*Leaf shape.*—Elliptic-ovate.

*Leaf arrangement.*—Opposite.

*Leaf division.*—Simple.

*Leaf number.*—Average of 8 (4 pairs) per lateral branch.

*Leaf base.*—Cuneate to oblique.

*Leaf apex.*—Cuspidate.

*Leaf margins.*—Serrated, average of 12 per side on a leaf 13 cm in length.

*Leaf venation.*—Pinnate, recessed on upper surface and raised on lower surface, color 145B to 145C on upper surface and 145C on lower surface.

*Leaf size.*—Average of 14 cm in length and 7.8 cm in width when mature.

*Leaf attachment.*—Petiolate.

*Leaf surface.*—Glabrous and dull on upper surface and finely puberulent on lower surface.

*Leaf color.*—Upper surface; 137A, lower surface; color between 138A and 138B.

*Petioles.*—Average of 3.5 cm in length and 4 mm in width, 144C in color, glabrous surface.

Inflorescence description:

*Inflorescence type.*—Terminal compound globose corymb comprised primarily of rotate shaped sterile flowers.

*Lastingness of inflorescence.*—Persistent but color is retained for about 3 to 4 weeks.

*Inflorescence number.*—One per lateral or sublateral stem if pinched.

*Inflorescence size.*—Average of 11 cm in depth and 21 cm in diameter.

*Flower number.*—About 400 sterile flowers and 20 fertile flowers per inflorescence.

*Flower fragrance.*—None.

*Flower aspect.*—Upright at stem terminus.

*Flower size.*—Sterile flowers; average of 2.5 cm in diameter and 4 mm in depth, fertile flowers; average of 3.5 mm in diameter and 7 mm in depth.

*Flower buds.*—Sterile flowers; average of 4 mm in length and 3 mm in width prior to opening, globose in shape, NN155C in color prior to opening, fertile flowers; average of 2 mm in width and diameter, globose in shape, 144B in color.

*Peduncles.*—For each complex corymb in inflorescence; average of 4 cm in length and 3 mm in width, 149D in color, glabrous surface, for individual corymbs; an average of 2 cm in length and 2 mm in width, 149D in color, glabrous surface, peduncle leaves; an average of 8 per inflorescence, up to 4.5 cm in length and 2.5 cm in width, elliptic in shape, same coloration and surface as stem leaves.

*Pedicels.*—Sterile flowers; an average of 1 cm in length and 1mm in width, typically held at about a 20 to 45° angle from vertical, NN155A in color, fertile flowers; 4 mm in length and 0.8 mm in width, NN155A in color, surface glabrous on all flowers.

*Petals.*—Sterile flowers; curled into eye zone, NN155C in color, 2 mm in diameter and 1.5 mm in depth, fertile flowers; 5, rotate in arrangement, ovate in shape, entire margin, acute apex, cuneate base, average of 1.2 mm in length and 1 mm in width, surface is glabrous and dull on both surfaces, color of upper and lower surface 144D.

*Sepals.*—Sterile flowers; average of 5, present on fertile flowers only, rotate in arrangement, rounded-diamond shaped, entire margin, broadly acute apex, cuneate base, average of 9 mm in length and width, surface is glabrous and dull on both surfaces, color of upper and lower surface on open flower is N155C, fertile flowers; 5, fused at base into campanulate base (2 mm in length and 1.5 mm in width), free segments; rotate in arrangement, glabrous and dull surface (both surfaces), ovate in shape, entire margin, acute apex, average of 2 mm in length and 1 mm in width, color 144B.

Reproductive organs: (fertile flowers):

*Stamens.*—Average of 3, anther is oblong in shape, about 1.2 mm in length and about 161B in color, filament is an average of 2 mm in length and N155B in color, pollen is minimal and 165B in color.

*Pistils.*—Average of 3, average of 2 mm in length and 0.7 mm in width, stigma is club-shaped and 199A in color, style is an average of 2 mm in length and N155B in color, ovary is about 1 mm in diameter and about N155A in color.

*Fruit and seed.*—Has not been observed under the conditions tested to date.

It is claimed:

1. A new and distinct cultivar of *Hydrangea* plant named 'White King' substantially as herein illustrated and described.

* * * * *